US009303001B2

(12) United States Patent
Zhang et al.

(10) Patent No.: US 9,303,001 B2
(45) Date of Patent: Apr. 5, 2016

(54) INTERMEDIATE OF STATIN DRUGS AND PREPARATION THEREOF

(75) Inventors: Shouhua Zhang, Dongguan (CN); Zhongqing Wang, Dongguan (CN); Zhonghua Luo, Dongguan (CN)

(73) Assignees: SUNSHINE LAKE PHARMA CO., LTD., Dongguan, Guangdong (CN); YICHANG HEC CHANGJIANG PHARMACEUTICAL CO., LTD., Yidu, Hubei (CN)

( * ) Notice: Subject to any disclaimer, the term of this patent is extended or adjusted under 35 U.S.C. 154(b) by 202 days.

(21) Appl. No.: 14/119,448

(22) PCT Filed: Jul. 19, 2012

(86) PCT No.: PCT/CN2012/078862
§ 371 (c)(1),
(2), (4) Date: Mar. 26, 2014

(87) PCT Pub. No.: WO2013/010488
PCT Pub. Date: Jan. 24, 2013

(65) Prior Publication Data
US 2014/0206883 A1    Jul. 24, 2014

(30) Foreign Application Priority Data
Jul. 19, 2011    (CN) .......................... 2011 1 0204524

(51) Int. Cl.
C07D 257/04    (2006.01)
C07D 319/06    (2006.01)
C07D 405/12    (2006.01)
C07F 7/18    (2006.01)
C07B 53/00    (2006.01)

(52) U.S. Cl.
CPC .............. *C07D 257/04* (2013.01); *C07B 53/00* (2013.01); *C07D 319/06* (2013.01); *C07D 405/12* (2013.01); *C07F 7/1852* (2013.01)

(58) Field of Classification Search
CPC .. C07D 257/04; C07D 319/06; C07D 405/12; C07F 7/1852
See application file for complete search history.

(56) References Cited

U.S. PATENT DOCUMENTS

| 6,875,867 | B2 | 4/2005 | Brodfuehrer et al. |
| 2012/0136151 | A1 | 5/2012 | Lee et al. |

FOREIGN PATENT DOCUMENTS

| CN | 100376682 | 3/2008 | |
| CN | 101613341 | 12/2009 | |
| CN | 101624390 | 1/2010 | |
| JP | 2003128629 | 5/2003 | |
| WO | WO 91/13876 A2 * | 9/1991 | ........... C07D 233/84 |
| WO | WO/03/027092 | 4/2003 | |
| WO | WO2008042876 | 4/2008 | |
| WO | WO 2010/140765 A2 | 12/2010 | |

OTHER PUBLICATIONS

Samii et al., Trifluoroacetoxysulphenylation of Unsaturated Nitrites and Transformation of the Adducts into Lactones, J. Chem. Soc., Perkin Trans. I, 1988, Issue 8, p. 2523-2531.
Christen et al., Biotransformation in organic synthesis: applications of yeast reduction in the synthesis of 3,5-dihydroxy esters of high optical purity, J. Chem. Soc., Chem Commun, 1988, Issue 4, p. 264-266.
Wolberg et al., Highly Regio- and Enantioselective Reduction of 3,5-Dioxocarboxylates, Angew. Chem. Int. Ed., 2000, vol. 39, Issue 23, p. 4306-4308.
Wolberg et al., Biocatalytic Reduction of β,δ-Diketo Esters: A Highly Stereoselective Approach to All Four Stereoisomers of a Chlorinated β,δ-Dihydroxy Hexanoate, 2001, Chem. Eur. J., vol. 7, Issue 21, pp. 4562-4571.
Kathawala et al., Stereoselective Reduction of δ-Hydroxy-β-ketoesters, Helv. Chim. Acta, 1986, vol. 69, Issue 4, p. 803-805.
Mislow et al., Stereoisomerism and Local Chirality, J. Am. Chem. Soc., 1984, vol. 106, Issue 11, p. 3319-3328.
Wang et al., Asymmetric Reduction of Tert-butyl (S)-6-chloro-5-hydroxy-3-oxo-hexanoate Catalyzed by Yeast Cells, Chemical Reaction Engineering and Technology, 2006, Issue 6, p. 554-559.
Evans et al., Directed Reduction of β-hydroxy Ketones Employing Tetramethylammonium Triacetoxyborohydride, J. Am. Chem. Soc., 1988, vol. 110, Issue 11, p. 3560-3578.
Evans et al., The Directed Reduction of β-hydroxy Ketones Employing Me4NHB(OAc)3, Tett. Lett., 1986, vol. 27, Issue 49, p. 5939-5942.
Chen et al., 1,3-Syn Diastereoselective Reduction of β-hydroxyketones Utilizing Alkoxydialkylboranes, Tett. Lett., 1987, vol. 28, Issue 2, p. 155-158.

* cited by examiner

*Primary Examiner* — Joseph Kosack
(74) *Attorney, Agent, or Firm* — Kam W. Law; Squire Patton Boggs (US) LLP

(57) ABSTRACT

The present invention relates to the field of pharmaceutical chemistry, specifically relates to a statin intermediate having formula I and preparation thereof.

(I)

$$R^1\text{-}S(O_2)\text{-}CH_2\text{-}CH(O\text{-}C(R^{11})(R^{12})\text{-}O)\text{-}CH_2\text{-}CH\text{-}CH_2\text{-}C(O)\text{-}O\text{-}R^2$$

The advantages of the method used to prepare the chiral sulfone intermediate having formula I are that a fluorophore is introduced at the beginning of the synthesis, and the intermediates are mostly solid, which enables quality control to be easily carried out.

18 Claims, No Drawings

INTERMEDIATE OF STATIN DRUGS AND PREPARATION THEREOF

CROSS-REFERENCE TO RELATED APPLICATIONS

This is a U.S. national stage application of the International Patent Application No. PCT/CN2012/078862, filed Jul. 19, 2012, which claims priority to Chinese Patent Application No. 201110204524.9, filed Jul. 19, 2011, both of which are incorporated herein by reference in their entirety.

FIELD OF THE INVENTION

The present invention relates to the field of pharmaceutical chemistry, specifically relates to statin intermediates and preparation thereof.

BACKGROUND OF THE INVENTION

Statin drugs are 3-hydroxy-3-methyl-glutaryl coenzyme A (HMG-CoA) reductase inhibitor. These drugs competitively inhibit the synthesis of HMG-CoA reductase from endogenous cholesterol, consequently block the metabolic pathway of mevalonate in cells and then lower the cholesterol levels in cells. Thereby, the drugs stimulate and increase the quantity and activity of low density lipoprotein (LDL) receptor on the surface of cells (mainly for live cells), increase the removal rate of cholesterol from Serum, and thereby lower the cholesterol level. Statin drugs can inhibit the synthesis of apolipoprotein B-100 in the liver, thereby reducing the synthesis and secretion of triglyceride and lipoprotein. In addition to the regulation of blood lipids, statin drugs can inhibit the vascular endothelial of inflammatory response, stabilize atheromatous plaque and improve the function of vascular endothelial if they are used early in patients having acute coronary syndrome. Statin drugs are also useful in delaying the extent of atherosclerosis, anti-inflammatory, protection of nerve and antithrombotic.

Some effective statin drugs include lovastatin, simvastatin, pravastatin, mevastatin, fluvastatin, atorvastatin, cerivastatin, pitavastatin and rosuvastatin, etc.

There are many methods of the preparation of statins. For example, WO2002098854 discloses a method of synthesizing the trans-substituted olefin bonds of statin drugs by Julia-Kocienski olefination, comprising reacting chiral sulfone with an aldehyde of a hydrophobic anchor or residue of a HMG-CoA reductase inhibitor.

Although there are currently many methods of the preparing statins, there are still needs for new improved methods for preparing statins or statin intermediates in this field.

SUMMARY OF THE INVENTION

Provided herein is a method of preparing a statin intermediate that differs from the prior art, wherein the statin intermediate is a chiral sulfone having formula I:

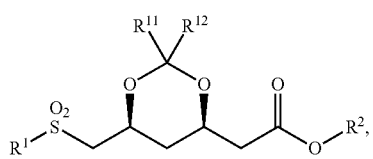

wherein $R^1$ is aryl or heterocyclyl, where the aryl or heterocyclyl is optionally unsubstituted or substituted with one or more substituents, where each of the substituents is independently alkyl, aryl, arylalkyl, halo, cycloalkyl, trifluoromethyl, nitro, cyano, trifluoromethoxy, amido, alkylcarbonyl, thiol or alkylthio;

$R^2$ is alkyl, cycloalkyl, arylalkyl, heterocyclyl, aryl or benzyloxycarbonyl; and each of $R^{11}$ and $R^{12}$ is independently alkyl.

The chiral sulfone can be used to prepare the intermediate of dihydroxy-acid (or its lactone) HMG-CoA reductase inhibitors. In some embodiments, each of $R^{11}$ and $R^{12}$ is independently methyl or ethyl.

In some embodiments, $R^1$ is

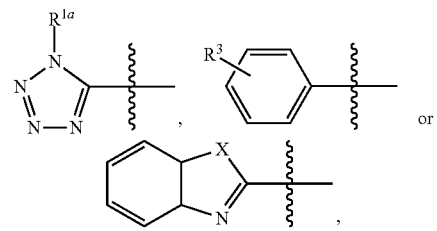

wherein:
$R^{1a}$ is alkyl, aryl, heteroaryl, arylalkyl or cycloalkyl;
$R^3$ is H, alkyl, aryl, arylalkyl, heteroaryl, trifluoromethyl, halo or nitro; and
X is O or S.

In some embodiments, $R^{1a}$ is $(C_1-C_4)$alkyl, aryl or arylalkyl. In other embodiments, $R^{1a}$ is phenyl. In some embodiments, $R^2$ is $(C_1-C_4)$alkyl, aryl or aryl-$(C_1-C_4)$alkyl. In other embodiments, $R^2$ is t-butyl or phenylisopropyl.

In some embodiments, the method of preparing chiral sulfone having formula I comprising: (a) reducing a dioxo compound having formula II with a reducing agent to form a dihydroxy compound of formula II-1; (b) protecting the hydroxy groups of the dihydroxy compound of formula II-1 to form a 1,3-dioxane compound of formula II-2; and (c) oxidizing the 1,3-dioxane compound of formula II-2 with an oxidizing agent to form the chiral sulfone,

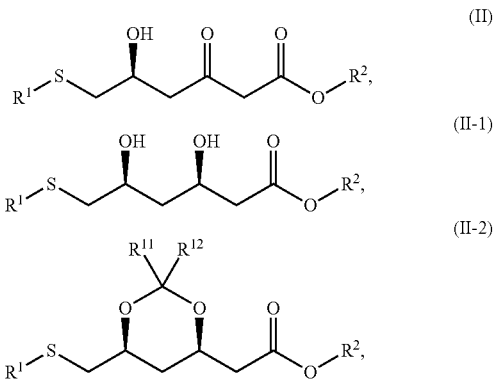

each of $R^1$, $R^2$, $R^{11}$ and $R^{12}$ is as defined herein.

In some embodiments, the reduction is a symmetric reduction or an asymmetric reduction. In other embodiments, the reducing agent is a symmetric reducing agent or an asymmetric reducing agent.

In some embodiments, the compound of formula II could be prepared by using the method, comprising: (d) the cyano compound of formula III and the thio compound of formula IV undergo a nucleophilic substitution reaction to form a compound of formula III-1; and (e) reacting the compound of formula III-1 with an ester of formula III-3 by Blaise reaction to form the dioxo compound of formula II. In some embodiments, in order to further increase the yield of reaction, the compound of formula III-1 is further protected with a hydroxyl-protecting agent to form the compound of formula III-2 before reacting with the ester of formula III-3 by Blaise reaction to form the dioxo compound of formula II,

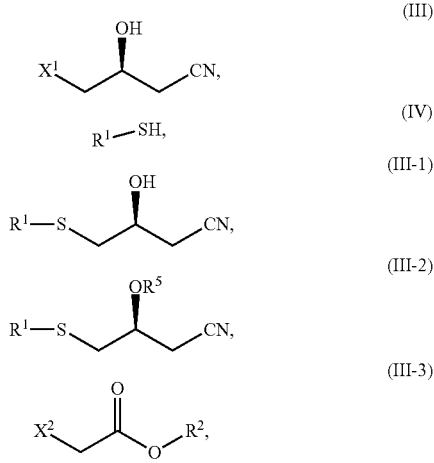

wherein each $R^1$ and $R^2$ is as defined herein;
each of $X^1$ and $X^2$ is independently a good leaving group; and
$R^5$ is a hydroxyl-protecting group which is methylsulfonyl, p-toluenesulfonyl, benzyl or

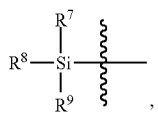

where each of $R^7$, $R^8$ and $R^9$ is independently alkyl.

In some embodiments, the good leaving group is F, Br, Cl, I, mesylate, tosylate or benzyl, etc. In other embodiments, $X^1$ is Cl. In some embodiments, $X^2$ is Br.

In some embodiments, each of $R^7$, $R^8$ and $R^9$ is independently methyl or t-butyl. In certain embodiments, each of $R^7$, $R^8$ and $R^9$ is independently methyl.

DETAILED DESCRIPTION OF THE INVENTION

Definitions and General Terminology

In the following description, all numbers disclosed herein are approximate values, regardless whether the word "about" or "approximate" is used in connection therewith. The value of each number may differ by 1%, 2%, 5%, 7%, 8%, 10%, 15% or 20%. Therefore, whenever a number having a value N is disclosed, any number having the value N+/−1%, N+/−2%, N+/−3%, N+/−5%, N+/−7%, N+/−8%, N+/−10%, N+/−15% or N+/−20% is specifically disclosed, wherein "+/−" refers to plus or minus. Whenever a numerical range with a lower limit, $R^L$, and an upper limit, $R^U$, is disclosed, any number falling within the range is specifically disclosed. In particular, the following numbers within the range are specifically disclosed: $R=R^L+k*(R^U-R^L)$, wherein k is a variable ranging from 1% to 100% with a 1% increment, i.e., k is 1%, 2%, 3%, 4%, 5%, . . . , 50%, 51%, 52%, . . . , 95%, 96%, 97%, 98%, 99%, or 100%. Moreover, any numerical range defined by two R numbers as defined above is also specifically disclosed.

As used herein the term "alkyl" or "alkane" refers to saturated linear or branched-chain groups contain 1-10 carbon atoms. Examples of alkyl include, but are not limited to, methyl, ethyl, propyl (including its isomers), butyl (including its isomers), pentyl (including its isomers), hexyl (including its isomers), heptyl (including its isomers), octyl (including its isomers), nonyl (including its isomers) or decyl (including its isomers). In some embodiments, the alkyl groups contain 1-6 carbon atoms. In other embodiments, the alkyl groups contain 1-4 carbon atoms. In certain embodiments, the alkyl group is methyl, ethyl, propyl (including its isomers) or butyl (including its isomers). In other embodiments, the alkyl group is methyl or t-butyl.

As used herein the term "cycloalkyl" refers to monocyclic ring or polycyclic ring contains 3-20 carbon atoms. In some embodiments, the cycloalkyl group is polycyclic ring contains 4-20 carbon atoms. In other embodiments, the cycloalkyl group is cyclopropyl, cyclopentyl, cyclohexyl or adamantyl.

As used herein the term "aryl" refers to monocyclic or bicyclic carbocyclic ring systems, wherein at least one ring in the system is aromatic. In some embodiments, the rings are fused with each other. In other embodiments, the aryl group is phenyl, naphthyl, indenyl, 1,2,3,4-tetrahydronaphthyl or indanyl. In certain embodiments, the aryl group is phenyl.

As used herein the term "heterocyclyl" refers to saturated heterocyclyl or heteroaryl contains at least one heteroatom. In some embodiments, the heteroatom is N, S, P or Si, or any oxidized form of S or P.

In some embodiments, the saturated heterocyclyl refers to a saturated monocycle having 3 to 8 ring members, which contains 1 to 4 nitrogen atoms, such as pyrrolealkyl, imidazolidinyl, piperidinyl, pyrrolinyl or piperazinyl; or a saturated monocycle having 3 to 8 ring members, which contains 1 to 2 oxygen atoms and 1 to 3 nitrogen atoms, such as morpholinyl; or a saturated monocycle having 3 to 8 ring members, which contains 1 to 2 sulfur atoms and 1 to 3 nitrogen atoms, such as thiazolylalkyl.

In some embodiments, the heteroaryl refers to an unsaturated monocycle having 5 to 8 ring members, which contains 1 to 4 nitrogen atoms, such as pyrrolyl, imidazolyl, pyrazolyl, 2-pyridinyl, 3-pyrazolyl, 4-pyridinyl, pyrimidinyl, pyrazinyl, pyridazinyl or triazolyl; examples of triazolyl include 4H-1, 2,4-triazolyl, 1H-1,2,3-triazolyl or 2H-1,2,3-triazolyl; or refers to an unsaturated monocycle having 5 to 8 ring members, which contains one oxygen atom, such as pyranyl, 2-furanyl or 3-furanyl, etc; or refers to an unsaturated monocycle having 5 to 8 ring members, which contains one sulfur atom, such as 2-thienyl or 3-thienyl, etc; or refers to an unsaturated monocycle having 5 to 8 ring members, which contains 1-2 oxygen atoms and 1-3 nitrogen atoms, such as oxazolyl, isoxazolyl or oxadiazolyl, etc; or refers to an unsaturated monocycle having 5 to 8 ring members, which contains 1-2 sulfur atoms and 1-3 nitrogen atoms, such as thiazolyl or thiadiazolyl.

In some embodiments, the heteroaryl refers to heteroaryl containing no nitrogen atom, some non-limiting examples of which include pyranyl, 2-furanyl, 3-furanyl, 2-thienyl, 3-thienyl, benzoruyl or benzothienyl, etc.

Description of Compounds of the Invention

Provided herein is a method of preparing a chiral sulfone having formula I as a statin intermediate, comprising: (a) reducing a dioxo compound having formula II with a reducing agent to form a dihydroxy compound of formula II-1; (b) protecting the hydroxy groups of the dihydroxy compound of formula II-1 to form a 1,3-dioxane compound of formula II-2; and (c) oxidizing the 1,3-dioxane compound of formula II-2 with an oxidizing agent to form the chiral sulfone.

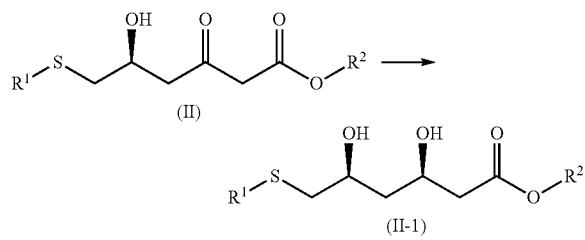

Step (a)

In some embodiments, step (a) occurs at the following conditions: a compound of formula II in a solvent is reduced with a hydride reagent. After the reaction mixture reacts for a certain time or until at least one of the reactants is undetectable, the product of formula II-1 is collected, isolated and/or purified from the reaction mixture, wherein each of $R^1$ and $R^2$ is as defined herein.

There is no limit on the solvent used in step (a), any solvent that can dissolve the reactants to a certain extent and does not inhibit the reduction reaction may be used in step (a). Wherein, the solvent is an alcohol solvent, an ether solvent, a halogenated solvent, an ester solvent, a ketone solvent, an aromatic hydrocarbon solvent or a combination thereof. In some embodiments, the alcohol solvent is methanol, ethanol, n-propanol, n-butanol or a combination thereof. In other embodiments, the ether solvent is tetrahydrofuran, ether, 1,4-dioxane, methyl tert-butyl ether, ethylene glycol dimethyl ether, diethylene glycol dimethyl ether, triethylene glycol dimethyl ether or a combination thereof. In some embodiments, the halogenated solvent is dichloromethane, 1,2-dichloroethane, chloroform or a combination thereof. In other embodiments, the ester solvent is ethyl acetate, isopropyl acetate or a combination thereof. In other embodiments, the ketone solvent is acetone, butanone or a combination thereof. In other embodiments, the aromatic hydrocarbon solvent is benzene, toluene, xylene or a combination thereof. In some embodiments, the solvent is a single solvent, such as methanol or tetrahydrofuran. In some embodiments, the solvent is a combination of the above solvent, such as a combination of alcohol and ether solvent. In other embodiments, the solvent is a combination of methanol and tetrahydrofuran.

Any hydride reagent that is suitable for reduction reactions can be used in step (a). In some embodiments, the hydride reagent is a metal hydride reagent, such as borohydride reagent. In other embodiments, the borohydride reagent is sodium borohydride or potassium borohydride, or a combination thereof. Any amount of hydride reagent that is suitable for reduction reactions can be used herein. In some embodiments, the amount used is 1 eq-5 eq, 1 eq-4 eq, 1 eq-3 eq, 1 eq-2.5 eq, 1.5 eq-2.1 eq or 1.9 eq-2.1 eq of the reactant.

In some embodiments, a reduction promoter can be added to step (a) and any reduction promoter that can promote a reduction reaction may be used in step (a). In some embodiments, the reduction promoter is borane reagent, such as borane, diborane, triethylborane or diethylmethoxyborane, etc. In other embodiments, the borane reagent is diethylmethoxyborane. Any amount of reduction promoter that is suitable for promoting reduction reactions can be used herein. In some embodiments, the amount of borane reagent used is 0-5 eq, 1 eq-5 eq, 2 eq-4 eq, 0.9 eq-1.5 eq or 1 eq-1.2 eq of the reactant.

Any temperature that is suitable for reduction reactions can be used in step (a). In some embodiments, the temperature of the reduction reaction is normally from about −80° C. to room temperature (normally at 25° C.). The reaction at the early stage or at the beginning occurs at a lower temperature, which is from about −80° C. to about −10° C., from about −80° C. to about −20° C., from about −80° C. to about −30° C., from about −80° C. to about −40° C., from about −80° C. to about −50° C., from about −80° C. to about −60° C. or from about −80° C. to about −70° C. The reaction occurs at a higher temperature after a complete reaction of the reactants, the temperature of which is from about −10° C. to room temperature, from about 0° C. to room temperature, from about 10° C. to room temperature or from about 20° C. to room temperature.

In the after treatment process of the reaction, an acid can be added to react with the hydride reagent completely and there is no limit to the acid used. Any acid that can react with a hydride reagent may be used in step (a). In some embodiments, the acid is an organic acid or an inorganic acid or a combination thereof. In other embodiments, the acid is hydrochloric acid, benzenesulfonic acid, hydrobromic acid, phosphoric acid, sulfuric acid, perchloric acid, acetic acid, oxalic acid, maleic acid, tartaric acid, citric acid, succinic acid, malonic acid, adipic acid, alginic acid, ascorbic acid, aspartic acid, benzoic acid, bisulfate acid, boric acid, butyric acid, camphoric acid, camphorsulfonic acid, cyclopentylpropionic acid, saccharic acid, lauryl sulfuric acid, ethanesulfonic acid, formic acid, fumaric acid, glucoheptonic acid, glycerophosphoric acid, gluconic acid, hemisulfuric acid, heptanoic acid, hexanoic acid, hydroiodic acid, 2-hydroxyethanesulfonic acid, lactobionic acid, lactic acid, lauric acid, malic acid, methanesulfonic acid, 2-naphthalene sulfonic acid, nicotinic acid, nitric acid, oleic acid, palmitic acid, pamoic acid, polygalacturonic acid, peroxydisulfuric acid, 3-phenylpropionic acid, picric acid, pivalic acid, propionic acid, stearic acid, thiocyanic acid, p-toluenesulfonic acid, undecylic acid, valeric acid or a combination thereof.

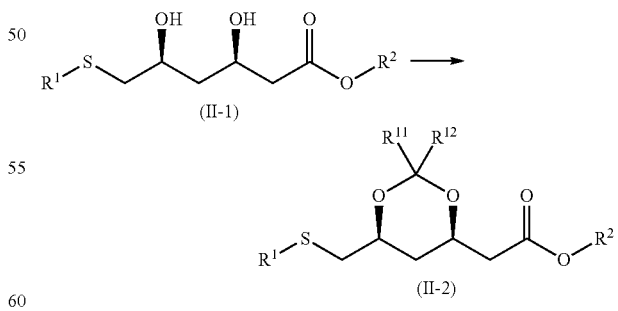

Step (b)

In some embodiments, step (b) occurs at the following conditions: a dihydroxy compound of formula II-1 in a solvent reacts with a compound of formula II-3 or formula II-4:

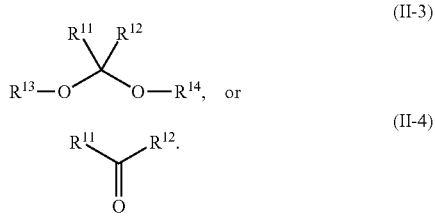

After the reaction mixture reacts for a certain time or until the dihydroxy compound of formula II-1 is undetectable, the product of formula II-2 is collected, isolated and/or purified from the reaction mixture, wherein each of $R^1$, $R^2$, $R^{11}$ and $R^{12}$ is as defined herein; and each of $R^{13}$ and $R^{14}$ is independently alkyl. In some embodiments, each of $R^{13}$ and $R^{14}$ is independently methyl, ethyl or propyl.

There is no limit on the solvent used in step (b), any solvent that can dissolve the reactants to a certain extent and does not inhibit reduction reactions may be used in step (b). In some embodiments, the solvent is an alcohol solvent, an ether solvent, a halogenated solvent, an ester solvent, a ketone solvent, an aromatic hydrocarbon solvent or a combination thereof. In some embodiments, the alcohol solvent is methanol, ethanol, n-propanol, n-butanol or combination thereof. In other embodiments, the ether solvent is tetrahydrofuran, ether, 1,4-dioxane, methyl tert-butyl ether, ethylene glycol dimethyl ether, diethylene glycol dimethyl ether, triethylene glycol dimethyl ether or combination thereof. In some embodiments, the halogenated solvent is dichloromethane, 1,2-dichloroethane, chloroform or combination thereof. In other embodiments, the ester solvent is ethyl acetate, isopropyl acetate or combination thereof. In other embodiments, the ketone solvent is acetone, butanone or combination thereof. In other embodiments, the aromatic hydrocarbon solvent is benzene, toluene, xylene or combination thereof. In some embodiments, the solvent is a single solvent. In other embodiments, the solvent is a combination of the above solvent. In some embodiments, the solvent is acetone, dichloromethane, tetrahydrofuran or combination thereof. In other embodiments, the solvent is acetone.

In some embodiments, an acid can be added as a catalyst in step (b) and there is no limit to the acid used. Any acid that can promote a protection reaction may be used in step (b). In some embodiments, the acid is an organic acid or an inorganic acid or a combination thereof. In other embodiments, the acid is hydrochloric acid, benzenesulfonic acid, hydrobromic acid, phosphoric acid, sulfuric acid, perchloric acid, acetic acid, oxalic acid, maleic acid, tartaric acid, citric acid, succinic acid, malonic acid, adipic acid, alginic acid, ascorbic acid, aspartic acid, benzoic acid, bisulfate acid, boric acid, butyric acid, camphoric acid, camphorsulfonic acid, cyclopentylpropionic acid, saccharic acid, lauryl sulfuric acid, ethanesulfonic acid, formic acid, fumaric acid, glucoheptonic acid, glycerophosphoric acid, gluconic acid, hemisulfuric acid, heptanoic acid, hexanoic acid, hydroiodic acid, 2-hydroxyethanesulfonic acid, lactobionic acid, lactic acid, lauric acid, malic acid, methanesulfonic acid, 2-naphthalene sulfonic acid, nicotinic acid, nitric acid, oleic acid, palmitic acid, pamoic acid, polygalacturonic acid, peroxydisulfuric acid, 3-phenylpropionic acid, picric acid, pivalic acid, propionic acid, stearic acid, thiocyanic acid, p-toluenesulfonic acid, undecylic acid, valeric acid or a combination thereof. In other embodiments, the acid is methanesulfonic acid, benzenesulfonic acid, p-toluenesulfonic acid or a combination thereof.

Any temperature that is suitable for protection reactions can be used herein. In some embodiments, the temperature of the protection reaction is from about 0° C. to the reflux temperature of the solvent, or is from about 0° C. to about 20° C., from about 0° C. to about 30° C., from about 0° C. to about 40° C. or from about 20° C. to about 40° C. In other embodiments, the temperature is at about room temperature (normally at 25° C.).

After the reaction is completed, an inorganic base or an organic base or a combination thereof can be added to the reaction system, wherein the inorganic base can be $NaHCO_3$, $KHCO_3$, $Na_2CO_3$, $K_2CO_3$, KOH, NaOH or a combination thereof; and wherein the organic base can be triethylamine, pyridine or a combination thereof

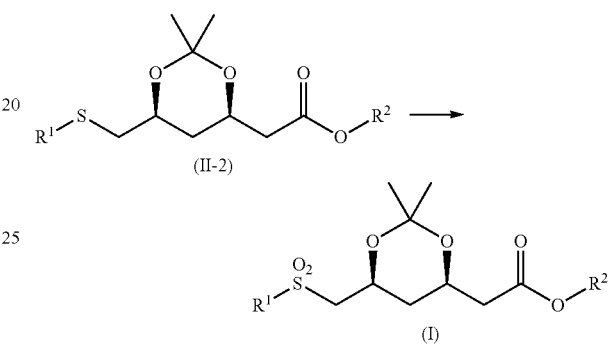

Step (c)

In some embodiments, step (c) occurs at the following conditions: a 1,3-dioxane compound of formula II-2 in a solvent is oxidized with an oxidizing agent. After the reaction mixture reacts for a certain time or until the compound of formula II-2 is undetectable, the product of formula I is collected, isolated and/or purified from the reaction mixture, wherein each of $R^1$ and $R^2$ is as defined herein.

Any oxidizing agent that is suitable for oxidation reactions can be used in step (c). In some embodiments, the oxidizing agent is $H_2O_2$; organic peroxy-acid, such as $CH_3COOOH$, $CF_3COOOH$ and perbenzoic acid, etc; halogen and halogen compounds, such as NaClO, $NaClO_4$ and periodic acid, etc; transition-metal compounds, such as $Cr_2O_3$, metal salts of dichromic acid and metal salts of permanganmic acid, etc; 3-chloroperbenzoic acid; $KHSO_5$; N-methyl morpholine-N-oxide; metal salts of monoperoxyphthalic acid such as magnesium salt of monoperoxyphthalic acid (MMPP); dimethyl-dioxirane or a combination thereof; or a combination of the above oxidizing agents.

There is no limit on the solvent used in step (c), any solvent that can dissolve the reactants to a certain extent and does not inhibit oxidation reactions may be used in step (c). In some embodiments, the solvent is an alcohol solvent, an ether solvent, a halogenated solvent, an ester solvent, a ketone solvent, an aromatic hydrocarbon solvent or a combination thereof. In some embodiments, the alcohol solvent is methanol, ethanol, n-propanol, n-butanol or combination thereof. In other embodiments, the ether solvent is tetrahydrofuran, ether, 1,4-dioxane, methyl tert-butyl ether, ethylene glycol dimethyl ether, diethylene glycol dimethyl ether, triethylene glycol dimethyl ether or combination thereof. In some embodiments, the halogenated solvent is dichloromethane, 1,2-dichloroethane, chloroform or combination thereof. In other embodiments, the ester solvent is ethyl acetate, isopropyl acetate or combination thereof. In other embodiments, the ketone solvent is acetone, butanone or combination thereof. In other embodiments, the aromatic hydrocarbon solvent is benzene, toluene, xylene or combination thereof. In some embodiments, the solvent is a single solvent. In other embodiments, the solvent is a combination of the above solvents, such as a combination of alcohol solvent and halogenated solvent. In some embodiments, the solvent is ethanol, isopropanol, dichloromethane or a combination thereof.

In some embodiments, an oxidation catalyst can be added to step (c) and there is no limit to the oxidizing catalyst. Any catalyst that can promote the oxidation reaction may be used in step (c). In other embodiments, the oxidation catalyst is metal, a salt thereof, or an oxide thereof, or a combination thereof. In some embodiments, the oxidation catalyst is Fe, W, V, Mo, Os or Ru, or a salt thereof, or an oxide thereof, or a combination thereof. In other embodiments, the oxidation catalyst is ammonium heptamolybdate, sodium tungstate, disodium molybdate, $FeCl_3$ or a combination thereof.

Any temperature that is suitable for oxidation reactions can be used in step (c). In some embodiments, the temperature of the oxidation reaction is from about 0° C. to about 50° C., from about 0° C. to about 20° C., from about 0° C. to about 30° C., from about 0° C. to about 40° C., from about 20° C. to about 40° C., or from about 40° C. to about 50° C.

In some embodiments, the dioxo compound of formula II can be prepared by reacting a cyano compound of formula III with a thio compound of formula IV,

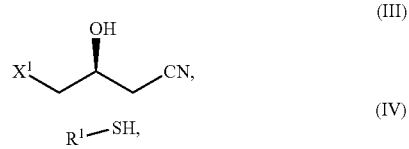

(III)

(IV)

wherein $X^1$ is a good leaving group; and $R^1$ is as defined herein. In some embodiments, $X^1$ is F, Br, Cl, I, mesylate, tosylate or benzyl.

In some embodiments, the dioxo compound of formula II can be prepared by the following method, comprising: (d) the compound of formula III and the compound of formula IV undergo a nucleophilic substitution reaction to form a compound of formula III-1; and (e) the compound of formula III-1 reacts with an ester of formula III-3 by Blaise reaction to form the dioxo compound of formula II,

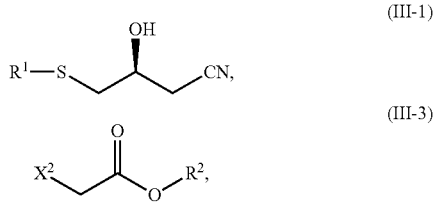

(III-1)

(III-3)

where $X^2$ is a good leaving group; and each of $R^1$ and $R^2$ is as defined herein. In some embodiments, $X^2$ is F, Br, Cl, I, mesylate, tosylate or benzyl.

In some embodiments, in order to increase the yield of the reaction, the compound of formula III-1 is protected with a hydroxyl-protecting agent to form the compound of formula III-2 before reacting with the ester of formula III-3 by Blaise reaction to form the dioxo compound of formula II,

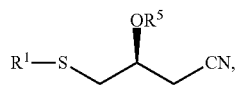

(III-2)

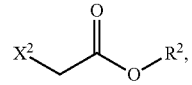

(III-3)

wherein each of $X^2$, $R^1$, $R^2$ and $R^5$ is as defined herein.

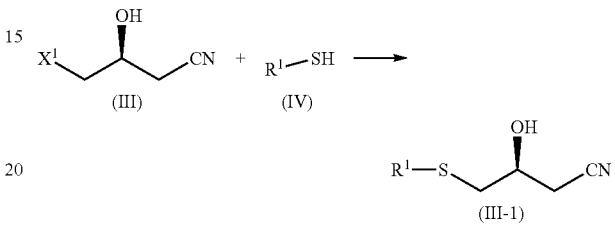

Step (d)

In some embodiments, the step (d) occurs at the following conditions: a compound of formula III in a solvent reacts with a compound of formula IV. After the reaction mixture reacts for a certain time or until the compound of formula III is undetectable, the product of formula III-1 is collected, isolated and/or purified from the reaction mixture, wherein each of $X^1$ and $R^1$ is as defined herein.

There is no limit on the solvent used in step (d), any solvent that can dissolve the reactants to a certain extent and does not inhibit the nucleophilic substitution reaction may be used in step (d). In some embodiments, the solvent is an alcohol solvent, an ether solvent, a halogenated solvent, an ester solvent, a ketone solvent, an aromatic hydrocarbon solvent, DMF (N,N-dimethylformamide), water or a combination thereof. In some embodiments, the alcohol solvent is methanol, ethanol, n-propanol, n-butanol or combination thereof. In other embodiments, the ether solvent is tetrahydrofuran, ether, 1,4-dioxane, methyl tert-butyl ether, ethylene glycol dimethyl ether, diethylene glycol dimethyl ether, triethylene glycol dimethyl ether or combination thereof. In some embodiments, the halogenated solvent is dichloromethane, 1,2-dichloroethane, chloroform or combination thereof. In other embodiments, the ester solvent is ethyl acetate, isopropyl acetate or combination thereof. In other embodiments, the ketone solvent is acetone, butanone or combination thereof. In other embodiments, the aromatic hydrocarbon solvent is benzene, toluene, xylene or combination thereof. In some embodiments, the solvent is a single solvent. In other embodiments, the solvent is a combination of the above solvent. In some embodiments, the solvent is water. In other embodiments, the solvent is a combination of a ketone solvent and water. In some embodiments, the solvent is a combination of DMF and water. In other embodiments, the solvent is a combination of methanol or ethanol and water.

While $X^1$ is F, Cl or Br, a catalytic amount of sodium iodide or potassium iodide or a combination thereof can be added as a catalyst to the reaction system.

In some embodiments, an inorganic base or an organic base or a combination thereof can be added to the reaction system in step (d), wherein the inorganic base is $NaHCO_3$, $KHCO_3$, Na$_2$CO$_3$, K$_2$CO$_3$, KOH, NaOH or a combination thereof; and wherein the organic base is triethylamine, pyridine or a combination thereof.

Any temperature that is suitable for the nucleophilic substitution reaction can be used herein. In some embodiments, the temperature of the nucleophilic substitution reaction is from about 0° C. to a reflux temperature of a solvent. In other embodiments, from about 0° C. to about 100° C., or from about 50° C. to about 100° C., from about 0° C. to about 30° C., from about 30° C. to about 50° C., or from about 50° C. to about 80° C., or at about 25° C., etc.

In some embodiments, step (e) occurs at the following conditions: a compound of formula III-1 or III-2 in a solvent reacts with an ester of formula III-3 by Blaise reaction in the presence of zinc powder. After the reaction mixture reacts for a certain time or until the compound of formula III-1 or III-2 is undetectable, the product of formula II is collected, isolated and/or purified from the reaction mixture,

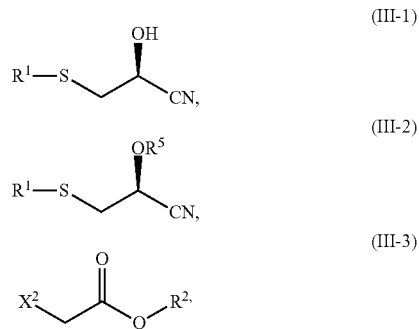

wherein X$^2$ is a good leaving group; and each of R$^1$, R$^2$ and R$^5$ is as defined herein. In some embodiments, X$^2$ is F, Br, Cl, I, mesylate, tosylate or benzyl Any solvent that can dissolve the reactants to a certain extent and does not inhibit the Blaise reaction may be used in step (e). In some embodiments, the solvent is an ether solvent such as tetrahydrofuran, diethyl ether, 1,4-dioxane, methyl tert-butyl ether, ethylene glycol dimethyl ether, diethylene glycol dimethyl ether, triethylene glycol dimethyl ether or a combination thereof.

Any reaction time that is suitable for the Blaise reaction can be used in step (e). In some embodiments, the reaction time is from about 1 hour to about 20 hours, from about 1 hour to about 15 hours, from about 1 hour to about 10 hours, or from about 1 hour to about 8 hours, or until the compound of formula III-1 or III-2 is undetectable.

In some embodiments, the compound of formula III-2 can be prepared according to the following method.

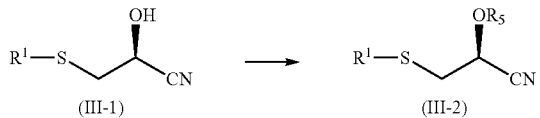

The compound of formula III-1 in a solvent reacts with a hydroxyl-protecting agent. After the reaction mixture reacts for a certain time or until the compound of formula III-1 is undetectable, the product of formula III-2 is collected, isolated and/or purified from the reaction mixture, wherein each of R$^1$ and R$^5$ is as defined herein. In some embodiments, the hydroxyl-protecting agent is R$^5$—Cl or hexamethyldisilazane (HMDS), wherein R$^5$ is as defined herein.

There is no limit on the solvent. Any solvent that can dissolve the reactants to a certain extent and does not inhibit the hydroxyl-protecting reaction may be used herein. In some embodiments, the solvent is an ether solvent, a halogenated solvent, an ester solvent, a ketone solvent, an aromatic hydrocarbon solvent or a combination thereof. In other embodiments, the ether solvent is tetrahydrofuran, ether, 1,4-dioxane, methyl tert-butyl ether, ethylene glycol dimethyl ether, diethylene glycol dimethyl ether, triethylene glycol dimethyl ether or a combination thereof. In some embodiments, the halogenated solvent is dichloromethane, 1,2-dichloroethane, chloroform or a combination thereof. In other embodiments, the ester solvent is ethyl acetate, isopropyl acetate or a combination thereof. In other embodiments, the ketone solvent is acetone, butanone or a combination thereof. In other embodiments, the aromatic hydrocarbon solvent is benzene, toluene, xylene or a combination thereof. In some embodiments, the solvent is a single solvent, such as dichloromethane or toluene. In other embodiments, the solvent is a combination of the above solvents.

In some embodiments, the hydroxyl-protecting reaction occurs in an alkaline environment in which triethylamine or pyridine or a combination thereof exists.

In some embodiments, if it is necessary for the hydroxyl-protecting reaction, 4-dialkylaminopyridine, such as 4-dimethylaminopyridine (DMAP), which can be added as a catalyst to promote the reaction. Any temperature that is suitable for the hydroxyl-protecting reaction can be used herein. In some embodiments, the temperature of the hydroxyl-protecting reaction is from about −10° C. to about 100° C., from about −10° C. to about 70° C., from about −10° C. to about 50° C., from about 0° C. to about 30° C. or from about 0° C. to about 25° C.

All of the above reaction steps can occur to a certain extent, for example, the percentage of the reactant consumed is about more than 20%, more than 30%, more than 40%, more than 50%, more than 70%, more than 80%, more than 90%, or more than 95%, or the reactant is undetectable or consumed completely. The reaction goes then on with after-treatment such as neutralization, collection, extraction, filtration, isolation, purification or a combination thereof. The extent of the reaction can be detected by conventional methods such as thin layer chromatography (TLC), high performance liquid chromatography (HPLC), gas chromatography (GC), and the like. The after-treatment of the reaction solution can be carried on by conventional methods, for example, an acid can be added to a basic reaction system to neutralize and terminate the reaction, or a base can be added to an acidic reaction system to neutralize and terminate the reaction. In some embodiments, the after-treatment can be evaporation of the solvent under reduced pressure to collect the crude product, which can be used in the next step directly. In certain embodiments, the after-treatment can be purifying the crude product and then using the purified product in the next step. In some embodiments, the after-treatment can be a purification step including adding water, a suitable organic solvent or a combination thereof to the crude product followed by extraction, distillation, crystallization, or separation by column chromatography, or the like.

In some embodiments, the chiral sulfone having formula I disclosed herein as an intermediate of statin drugs can be used to prepare dihydroxy-acid (or its lactone) HMG-CoA reductase inhibitors including lovastatin, simvastatin, pravastatin, mevastatin, fluvastatin, atorvastatin, cerivastatin, pitavastatin and rosuvastatin, etc.

The methods of preparing the chiral sulfone having formula I as an intermediate of statin drugs is described herein. The advantages are that a fluorophore is introduced at the beginning of the synthesis, and the intermediates are mostly solid, which enables quality control to be easily carried out. Further, the materials used for preparation are inexpensive.

EXAMPLES

Disclosed herein are methods of preparing intermediates of statin drugs, which can be carried out by the skilled artisan in the field, who based on the disclosure of this specification can improve the parameters or conditions of the processes disclosed herein. All substitutions and changes that are similar to the parameters or conditions disclosed herein are deemed to be disclosed by the present invention, and are obvious to the skilled artisan in the field. The methods of the present invention are described by the embodiments disclosed herein. The skilled artisan in the field can alter or properly change and combine the methods and applications based on the content, spirit and scope of the present invention, to carry out or apply the methods and applications of the present invention. The reagents used in the present invention can be purchased commercially or prepared by the methods described herein.

In order to make the skilled artisan in the field to have a better understanding of the present invention, disclosed herein are further description of the present invention with the following non-limiting examples.

Example 1

Preparation of (S)-3-hydroxy-4-(1-phenyltetrazole-5-sulfanyl)butyronitrile

To an aqueous solution of methanol (180 g) was added 1-phenyl-5-mercaptotetrazole (32.7 g) and sodium iodide (1.25 g). After the mixture was stirred to dissolve the reactants, an aqueous solution of sodium hydroxide (8.8 g sodium hydroxide dissolved in 70 g water) was added dropwise into the solution. After stirred for about 30 minutes at room temperature, the reaction mixture was heated to about 70° C. Then (S)-4-chloro-3-hydroxybutyronitrile (20 g) was added dropwise into the mixture. After stirred at about 70° C. for 12 hours to 13 hours, the methanol was evaporated, and the reaction mixture was cooled to room temperature. The reaction mixture was filtered and the filter cake was washed with water, then dried to give the product as a white solid (27.8 g, 95%).

Example 2

Preparation of (S)-3-hydroxy-4-(1-phenyltetrazole-5-sulfanyl)butyronitrile

To 200 g of water was added 1-phenyl-5-mercaptotetrazole (32.7 g) and sodium iodide (1.25 g). After the mixture was stirred to dissolve the reactants, an aqueous solution of sodium hydroxide (8.8 g sodium hydroxide dissolved in 70 g water) was added dropwise into the solution. After stirred for about 30 minutes at room temperature, the reaction mixture was heated to about 70° C. Then (S)-4-chloro-3-hydroxybutyronitrile (18.2 g) was added dropwise into the mixture. After stirred at about 70° C. for 12 hours to 13 hours, the methanol was evaporated, and the reaction mixture was cooled to room temperature. The reaction mixture was filtered and the filter cake was washed with water, then dried to give the product as a white solid (35.7 g).

Example 3

Preparation of (S)-3-hydroxy-4-(1-phenyltetrazole-5-sulfanyl)butyronitrile

To 200 g of N,N-dimethylformamide was added triethylamine (42.5 g) and sodium iodide (2.4 g). After the mixture was stirred to dissolve the reactants, a solution of 1-phenyl-5-mercaptotetrazole (69.0 g) in DMF was added. After stirred for about 30 minutes at room temperature, (S)-4-chloro-3-hydroxybutyronitrile (38.6 g) was added dropwise into the mixture, and the reaction mixture was heated to about 90° C. and stirred for 15 hours to 16 hours. After the reaction mixture was cooled to room temperature, 800 g water was added and then it was stirred for about 1 hour. The reaction mixture was filtered and the filter cake was washed with water, and then dried to give the product as a white solid (73.1 g).

Example 4

Preparation of (S)-3-trimethylsiloxy-4-(1-phenyltetrazole-5-sulfanyl)butyronitrile To 245 ml of dichloromethane was added (S)-3-hydroxy-4-(1-phenyltetrazole-5-sulfanyl)butyronitrile (49 g), triethylamine (24.6 g) and 4-dimethylaminopyridine (1.15 g) while it was stirred. Then the reaction mixture was cooled to 0° C. After trimethyl chlorosilane (24.4 g) was added dropwise, the reaction mixture was stirred at 0° C.-25° C. until TLC indicated that the reaction was complete. After the reaction mixture was cooled to 0° C., 245 g water was added dropwise. After stirred at room temperature for about 30 minutes, the mixture was separated. The aqueous layer was discarded and the organic layer was evaporated to dryness under reduced pressure to give a colorless oil which was directly used for the next step.

Example 5

Preparation of (S)-3-trimethylsiloxy-4-(1-phenyltetrazole-5-sulfanyl)butyronitrile To 250 ml of toluene was added (S)-3-hydroxy-4-(1-phenyltetrazole-5-sulfanyl)butyronitrile (50 g), triethylamine (67.7 g) and 4-dimethylaminopyridine (1.17 g) while it was stirred. After the reaction mixture was cooled to 0° C.-5° C., trimethyl chlorosilane (62.4 g) was added dropwise over about 60 minutes. Then the reaction mixture was stirred at 5° C.-25° C. for 1 hour to 2 hours until TLC indicated that the reaction was complete. Then 245 g water was added dropwise to the mixture at about 5° C. After stirred at room temperature for about 30 minutes, the reaction mixture was separated. The aqueous layer was discarded and the organic layer was evaporated to dryness under reduced pressure to give a colorless oil which was directly used for the next step.

Example 6

Preparation of (S)-3-trimethylsiloxy-4-(1-phenyltetrazole-5-sulfanyl)butyronitrile To 50 ml of tetrahydrofuran was added (S)-3-hydroxy-4-(1-phenyltetrazole-5-sulfanyl)butyronitrile (50 g) and triethylamine (67.7 g) while it was stirred. After the reaction mixture was cooled to 0° C.-5° C., trimethyl chlorosilane (62.4 g) was added dropwise over about 60 minutes. Then the reaction mixture was stirred at 5° C.-25° C. for 1 hour to 2 hours until TLC indicated that the reaction was complete. Then 100 ml 10% ammonium chloride aqueous solution was added dropwise to the reaction mixture at about 5° C. over 1 hour. Then 300 ml ethyl acetate was added for extraction and the organic layer was separated, dried over anhydrous $Na_2SO_4$, evaporated to dryness under reduced pressure to give a colorless oil which was directly used for the next step.

Example 7

Preparation of (S)-3-trimethylsiloxy-4-(1-phenyltetrazole-5-sulfanyl)butyronitrile (S)-3-Hydroxy-4-(1-phenyltetrazole-5-sulfanyl)butyronitrile (49 g), triethylamine (24.6 g) and 4-dimethylaminopyridine (1.15 g) was added to 245 ml dichloromethane. The reaction mixture was cooled to 0° C. while it was stirred. After trimethyl chlorosilane (24.4 g) was added dropwise to the reaction mixture, it was stirred at 5° C.-25° C. until TLC indicated that the reaction was complete. Then it was cooled to about 0° C. and 245 g water was added dropwise. After stirred at room temperature for about 30 minutes, the reaction mixture was separated. The aqueous layer was discarded and the organic layer was evaporated to dryness under reduced pressure to give a colorless oil which was directly used for the next step.

Example 8

Preparation of (S)-3-trimethylsiloxy-4-(1-phenyltetrazole-5-sulfanyl)butyronitrile To a flask was added (S)-3-hydroxy-4-(1-phenyltetrazole-5-sulfanyl)-butyronitrile (52.3 g), hexamethyldisilazane (32.3 g) and 300 ml toluene. The reaction mixture was cooled to 80° C.±3° C. and stirred until TLC indicated that the reaction was complete. Then the reaction mixture was cooled to about 40° C. The organic layer was washed and evaporated to remove the solvent under reduced pressure to give a colorless oil which was directly used for the next step.

Example 9

Preparation of tert-butyl (5S)-5-hydroxy-3-oxo-6-(1-phenyltetrazole-5-sulfanyl) hexanoate To 100 ml of tetrahydrofuran was added (S)-3-trimethylsiloxy-4-(1-phenyltetrazole-5-sulfanyl)butyronitrile (19 g) and zinc power (7.6 g) under $N_2$, followed by addition of a catalytic amount of methanesulfonic acid and the reaction mixture was allowed to reflux for 1 hour to 2 hours. The reaction mixture was cooled to 50° C.-60° C. and tert-butyl bromoacetate (22.2 g) was added. Then the reaction mixture was stirred at 50° C.-60° C. for 8 hours to 15 hours and adjusted the pH to about 4 with 3 M hydrochloric acid at about 0° C. and then evaporated to remove tetrahydrofuran and a trace amount of water. The mixture was extracted with dichloromethane, and the separated organic layer was concentrated to provide a crude product of tert-butyl (5S)-5-hydroxy-3-oxo-6-(1-phenyltetrazole-5-sulfanyl)hexanoate (18.3 g).

Example 10

Preparation of tert-butyl (5S)-5-hydroxy-3-oxo-6-(1-phenyltetrazole-5-sulfanyl) hexanoate To 100 ml of tetrahydrofuran was added zinc power (7.6 g) and methanesulfonic acid (0.76 g) under $N_2$, it was refluxed for 15 minutes. Tert-butyl bromoacetate (22.2 g) was added slowly, and then a combination of (S)-3-trimethylsiloxy-4-(1-phenyltetrazole-5-sulfanyl)butyronitrile (19 g) and 200 ml tetrahydrofuran was added over about 1 hour. The reaction mixture was stirred for another 40 minutes to 60 minutes until TLC indicated that the reaction was complete. Then it was cooled to 0° C. After 10% hydrochloric acid (40 ml) was added, the reaction was stirred for about 1 hour. The mixture was extracted with ethyl acetate (200 ml), and the separated organic layer was dried over anhydrous $Na_2SO_4$, concentrated under reduced pressure to provide a crude product of tert-butyl (5S)-5-hydroxy-3-oxo-6-(1-phenyltetrazole-5-sulfanyl)hexanoate (17.5 g).

Example 11

Preparation of tert-butyl (5S)-5-hydroxy-3-oxo-6-(1-phenyltetrazole-5-sulfanyl) hexanoate To a flask was added tetrahydrofuran (40 ml), zinc power (8.2 g) and methanesulfonic acid (0.19 g) and the reaction mixture was refluxed for about 1 hour. A solution of (S)-3-trimethylsiloxy-4-(1-phenyltetrazole-5-sulfanyl)butyronitrile (12.8 g) in 60 ml tetrahydrofuran and tert-butyl bromoacetate (18.7 g) was added dropwise slowly. The reaction mixture was stirred for another 4 hours to 6 hours until (S)-3-trimethylsiloxy-4-(1-phenyltetrazole-5-sulfanyl)butyronitrile consumed completely. The reaction mixture was filtered. The filtrate was acidified with a certain amount of acetic acid (18.4 g) and water (50 ml), and reacted for 6 hours until the intermediate of zinc salt disappeared. The mixture was evaporated to remove tetrahydrofuran under reduced pressure followed by extracted with 60 ml toluene. The separated organic layer was concentrated under reduced pressure to provide a crude product of tert-butyl (5S)-5-hydroxy-3-oxo-6-(1-phenyltetrazole-5-sulfanyl)hexanoate (11.6 g).

Example 12

Preparation of tert-butyl (3R,5S)-3,5-dihydroxy-3-oxo-6-(1-phenyltetrazole-5-sulfanyl)hexanoate To a flask was added tert-butyl (5S)-5-hydroxy-3-oxo-6-(1-phenyltetrazole-5-sulfanyl)hexanoate (16 g), 50 ml methanol and 150 ml tetrahydrofuran. After the mixture was stirred to dissolve the reactants, a solution of diethylmethoxyborane in tetrahydrofuran (46.5 ml, 1 M) was added dropwise into the reaction mixture under $N_2$ at from −70° C. to −80° C. over about 1 hour. After sodium borohydride (1.9 g) was added to the reaction mixture at this temperature, the reaction mixture was stirred at from −70° C. to −80° C. for about 3 hours. After TLC indicated that the starting material was consumed completely, the reaction mixture was warmed to room temperature slowly. After acetic acid (10 ml) was added, the reaction mixture was stirred at room temperature for about 30 minutes, concentrated to remove most of the solvent under reduced pressure, and extracted with a mixture of water (100 ml) and ethyl acetate (100 ml). The organic layer was washed with saturated sodium bicarbonate aqueous solution (80 ml). Then 2M sodium hydroxide aqueous solution (21 ml) and 30% hydrogen peroxide aqueous solution (45 ml) was added to the organic layer, the mixture was stirred until TLC indicated that boric acid ester was almost consumed completely. The reaction mixture was separated, and the separated organic layer was washed with saturated sodium bisulfate aqueous solution and water, dried over anhydrous $Na_2SO_4$, and evaporated to dryness under reduced pressure to give a light yellow oil which was directly used for the next step.

Example 13

Preparation of tert-butyl (3R,5S)-3,5-dihydroxy-3-oxo-6-(1-phenyltetrazole-5-sulfanyl)hexanoate To a 250 ml flask was added tert-butyl (5S)-5-hydroxy-3-oxo-6-(1-phenyltetrazole-5-sulfanyl)hexanoate (16 g) and 150 ml tetrahydrofuran. After the mixture was stirred to dissolve the reactants, a solution of diethylmethoxyborane in tetrahydrofuran (46.5 ml, 1M) was added dropwise into the reaction mixture under $N_2$ at about −70° C. over about 1 hour. Sodium borohydride (1.9 g) was added to the reaction mixture at this temperature, after the temperature was stable, 50 ml methanol was added and it was stirred at from −60° C. to −70° C. for about 3 hours. After TLC indicated that the starting material was consumed completely, the reaction mixture was warmed to −15° C. and acetic acid (10 ml) was added. The reaction mixture was stirred at room temperature for about 30 minutes, concentrated to remove most of the solvent under reduced pressure. Then it was extracted with a mixture of water (100 ml) and ethyl acetate (100 ml), and the organic layer was washed with saturated sodium bicarbonate aqueous solution (80 ml). Then 30% hydrogen peroxide aqueous solution (45 ml) was added to the organic layer, the mixture was stirred until TLC indicated that boric acid ester was almost consumed completely. The reaction mixture was separated, and the separated organic layer was washed with saturated sodium bisulfate aqueous solution and water, dried over anhydrous $Na_2SO_4$, and evaporated to dryness under reduced pressure to give a light yellow oil which was directly used for the next step.

Example 14

Preparation of tert-butyl (3R,5S)-6-(1-phenyltetrazole-5-sulfanyl)-3,5-oxo-isopropylidene-3,5-dihydroxy-hexanoate A catalytic amount of methanesulfonic acid was added to a solution of tert-butyl (3R,5S)-3,5-dihydroxy-3-oxo-6-(1-phenyltetrazole-5-sulfanyl)hexanoate and 2,2-dimethoxypropane (1.5 eq) in acetone. The reaction mixture was stirred at room temperature for about 3 hours. After TLC indicated that the starting material was consumed completely, triethylamine was added. After the reaction mixture was evaporated to dryness under reduced pressure, toluene and saturated sodium bicarbonate aqueous solution was added. The mixture was stirred for 30 minutes, then held and separated. The separated organic layer was concentrated under reduced pressure to give a brown oil which was directly used for the next oxidation reaction.

Example 15

Preparation of tert-butyl (3R,5S)-6-(1-phenyltetrazole-5-sulfanyl)-3,5-oxo-isopropylidene-3,5-dihydroxy-hexanoate A catalytic amount of methanesulfonic acid was added to a solution of tert-butyl (3R,5S)-3,5-dihydroxy-3-oxo-6-(1-phenyltetrazole-5-sulfanyl) hexanoate and 2,2-dimethoxypropane (5.3 g) in 50 ml acetone. The reaction mixture was stirred at room temperature for about 3 hours. After TLC indicated that the starting material was consumed completely, triethylamine was added. After the mixture was evaporated to dryness under reduced pressure, toluene and saturated sodium bicarbonate aqueous solution was added, and the mixture was stirred for 30 minutes. Then it was held and separated and the separated organic layer was concentrated under reduced pressure to give a brown oil which was directly used for the next oxidation reaction.

Example 16

Preparation of tert-butyl (3R,5S)-6-(1-phenyltetrazole-5-sulfonyl)-3,5-oxo-isopropylidene-3,5-dihydroxy-hexanoate To the brown oil of tert-butyl (3R,5S)-6-(1-phenyltetrazole-5-sulfanyl)-3,5-oxo-isopropylidene-3,5-dihydroxy-hexanoate prepared above, was added isopropanol (37 g) and ammonium heptamolybdate (2.38 g) at room temperature. Then 30% Hydrogen peroxide aqueous solution (21.6 g) was added to the reaction mixture and it was stirred at room temperature for 7 hours until TLC indicated that the sulfoxide disappeared. The mixture was heated to 50° C. and stirred for about 1 hour. Then it was cooled to about 25° C. slowly and stirred for about 1 hour. The mixture was filtered and dried to give a white solid (15.5 g).

Example 17

Preparation of tert-butyl (3R,5S)-6-(1-phenyltetrazole-5-sulfonyl)-3,5-oxo-isopropylidene-3,5-dihydroxy-hexanoate To the brown oil of tert-butyl (3R,5S)-6-(1-phenyltetrazole-5-sulfanyl)-3,5-oxo-isopropylidene-3,5-dihydroxy-hexanoate prepared above, was added 45 ml isopropanol, 10 ml dichloromethane and ammonium heptamolybdate (4.2 g) at room temperature. The mixture was cooled to 20° C.-25° C., 30% hydrogen peroxide aqueous solution (47.9 g) was added to the mixture and it was stirred at room temperature (30° C.±5° C.) for 7 hours to 9 hours until TLC indicated that the sulfoxide disappeared. The reaction mixture was still stirred at this temperature for about 3 hours and evaporated to remove dichloromethane. After that, the mixture was heated to about 50° C. and stirred for about 1 hour. Then it was cooled to about 25° C. slowly and stirred for about 1 hour. The mixture was filtered and the filter cake was washed with saturated sodium bicarbonate and an aqueous solution of isopropanol, and dried to give the product (15.0 g).

Example 18

Preparation of tert-butyl (3R,5S)-6-(1-phenyltetrazole-5-sulfonyl)-3,5-oxo-isopropylidene-3,5-dihydroxy-hexanoate To the brown oil of tert-butyl (3R,5S)-6-(1-phenyltetrazole-5-sulfanyl)-3,5-oxo-isopropylidene-3,5-dihydroxy-hexanoate prepared above, was added 50 ml ethanol and ammonium heptamolybdate (4.2 g) at room temperature. The reaction mixture was cooled to 20° C.-25° C., 30% hydrogen peroxide aqueous solution (47.9 g) was added to the mixture and it was stirred at room temperature for 7 hours to 9 hours until TLC indicated that the sulfoxide disappeared. The reaction mixture was still stirred at this temperature for about 3 hours and then it was heated to about 50° C. and stirred for about 1 hour. After that, 50 g water was added and the mixture was stirred for about 1 hour. Then it was cooled to about 25° C. slowly and stirred for about 1 hour. The mixture was filtered and the filter cake was dried to give the product (16.0 g).

All above are just some of the better embodiments of the present invention. A skilled artisan in the field can conduct some improvements and modifications without departing from the premise of principle of the present invention, which are also deemed to be within the scope of the present invention.

We claim:

1. A method of preparing a chiral sulfone having formula I as a statin intermediate, comprising: (a) reducing a dioxo compound having formula II with a reducing agent to form a dihydroxy compound of formula II-1; (b) protecting the hydroxy groups of the dihydroxy compound of formula II-1 to form a 1,3-dioxane compound of formula II-2; and (c) oxidizing the 1,3-dioxane compound of formula II-2 with an oxidizing agent to form the chiral sulfone,

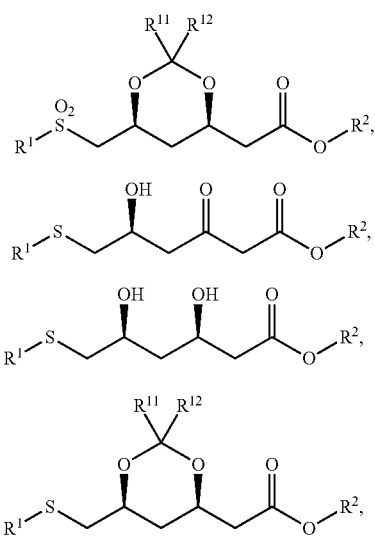

wherein $R^1$ is aryl or heterocyclyl, where the aryl or heterocyclyl is optionally unsubstituted or substituted with one or more substituents, where each of the substituents is independently alkyl, aryl, arylalkyl, halo, cycloalkyl, trifluoromethyl, nitro, cyano, trifluoromethoxy, amido, alkylcarbonyl, thiol or alkylthio;
each of $R^{11}$ and $R^{12}$ is independently alkyl; and
$R^2$ is alkyl, cycloalkyl, arylalkyl, heterocyclyl, aryl or benzyloxycarbonyl.

2. The method of claim 1, wherein the reducing agent is a hydride reagent, a borohydride reagent or a combination thereof.

3. The method of claim 2, wherein the hydride reagent is a metal hydride reagent and the borohydride reagent is sodium borohydride, potassium borohydride or a combination thereof.

4. The method of claim 1, wherein in step (b), the dihydroxy compound of formula II-1 reacts with a compound of formula II-3 or formula II-4,

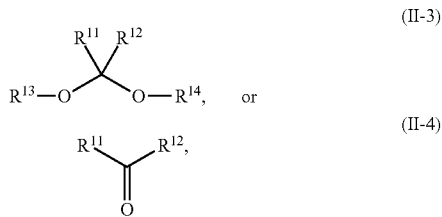

wherein each of $R^{13}$ and $R^{14}$ is independently alkyl.

5. The method of claim 1, wherein the oxidizing agent is $H_2O_2$, $CH_3COOOH$, $CF_3COOOH$, perbenzoic acid, NaClO, $NaClO_4$, periodic acid, $Cr_2O_3$, metal salts of dichromic acid, metal salts of permanganic acid, 3-chloroperbenzoic acid, $KHSO_5$, N-methyl morpholine-N-oxide, magnesium salt of monoperoxyphthalic acid, dimethyldioxirane or a combination thereof.

6. The method of claim 5, wherein step (c) occurs in the presence of a catalyst, where the catalyst is Fe, W, V, Mo, Os or Ru, or a salt thereof, or an oxide thereof, or a combination thereof, or the catalyst is ammoinum heptamolybdate, sodium tungstate, disodium molybdate, $FeCl_3$ or a combination thereof.

7. The method of claim 1, further comprising: (d) preparing the dioxo compound of formula II by reacting a cyano compound of formula III with a thio compound of formula IV,

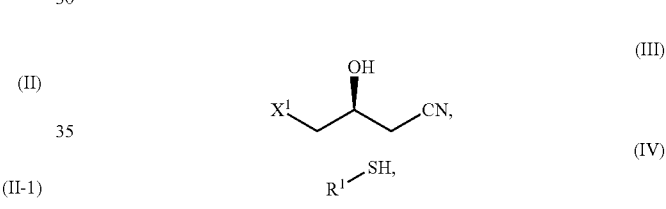

wherein $X^1$ is a good leaving group which is F, Br, Cl, I, mesylate, tosylate or benzyl.

8. The method of claim 7, wherein the cyano compound of formula III reacts with the thio compound of formula IV in the presence of an inorganic base or an organic base, wherein the inorganic base is $NaHCO_3$, $KHCO_3$, $Na_2CO_3$, $K_2CO_3$, KOH, NaOH or a combination thereof; and wherein the organic base is triethylamine, pyridine or a combination thereof.

9. The method of claim 7, wherein in step (d), the cyano compound and the thio compound undergo a nucleophilic substitution reaction to form a compound of formula III-1; and the method further comprises: (e) reacting the compound of formula III-1 with an ester of formula III-3 by Blaise reaction to form the dioxo compound of formula II,

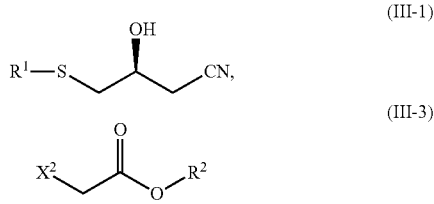

where $X^2$ is a good leaving group which is F, Br, Cl, I, mesylate, tosylate or benzyl.

10. The method of claim 9, wherein in step (e), the compound of formula III-1 is protected with a hydroxyl-protecting agent to form the compound of formula III-2 before reacting with the ester of formula III-3 by Blaise reaction to form the dioxo compound of formula II, where the hydroxyl-protecting agent is $R^5$—Cl or hexamethyldisilazane,

 (III-2)

wherein $R^5$ is a hydroxyl-protecting group which is methylsulfonyl, p-toluenesulfonyl, benzyl or

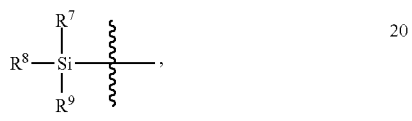, where each of $R^7$, $R^8$ and $R^9$ is independently alkyl.

11. The method of claim 1, wherein
$R^1$ is

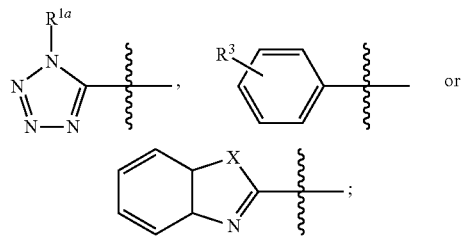

$R^{1a}$ is H, alkyl, aryl, arylalkyl or cycloalkyl;
$R^3$ is H, alkyl, aryl, arylalkyl, trifluoromethyl, halo or nitro; and
X is O or S.

12. The method of claim 1, wherein
$R^1$ is

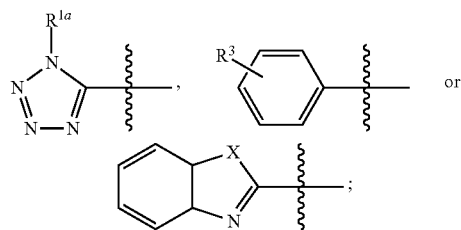

$R^2$ is $(C_1-C_4)$alkyl, aryl or aryl-$(C_1-C_4)$alkyl;
each of $R^{11}$ and $R^{12}$ is independently methyl or ethyl;
$R^{1a}$ is $(C_1-C_4)$alkyl, aryl or arylalkyl; and
$R^3$ is H, alkyl, aryl, arylalkyl, heterocyclyl, trifluoromethyl, halo or nitro.

13. The method of claim 12, wherein
$R^1$ is

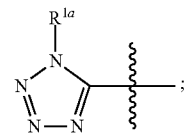;

$R^2$ is t-butyl or phenylisopropyl; and
$R^{1a}$ is phenyl.

14. The method of claim 9, wherein $X^1$ is Cl; and $X^2$ is Br.
15. The method of claim 4, wherein each of $R^{13}$ and $R^{14}$ is independently methyl.
16. The method of claim 10, wherein $R^5$ is

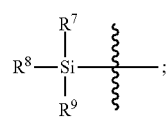;

and each of $R^7$, $R^8$ and $R^9$ is independently methyl or t-butyl.

17. A compound of formula II, formula III-1, or formula III-2:

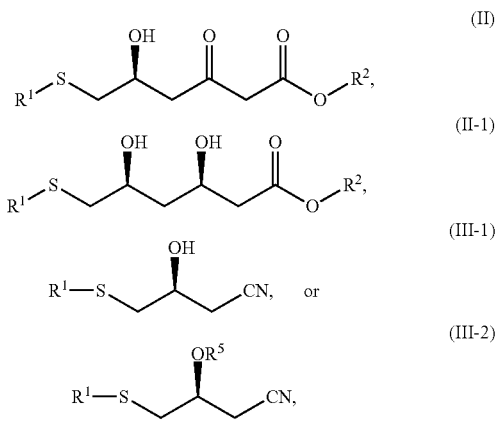

wherein each $R^1$ is independently heterocyclyl, where the heterocyclyl is optionally unsubstituted or substituted with one or more suitable substituents, where each of the substituents is independently alkyl, aryl, arylalkyl, halo, cycloalkyl, trifluoromethyl, nitro, cyano, trifluoromethoxy, amido, alkylcarbonyl, thiol or alkylthio;
each $R^2$ is independently alkyl, cycloalkyl, arylalkyl, heterocyclyl, aryl or benzyloxycarbonyl; and
$R^5$ is a hydroxyl-protecting group which is methylsulfonyl, p-toluenesulfonyl, benzyl or

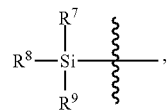, where each of $R^7$, $R^8$ and $R^9$ is independently alkyl.

18. A compound of formula II, formula II-1, formula III-1, or formula III-2:

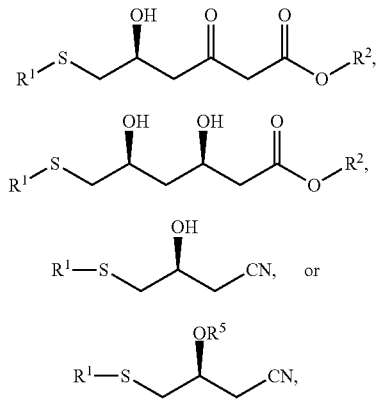

(II)

(II-1)

(III-1)

(III-2)

wherein each $R^1$ is independently

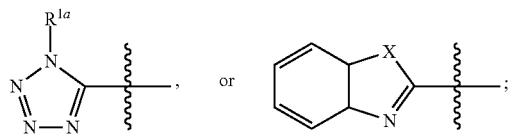

where the

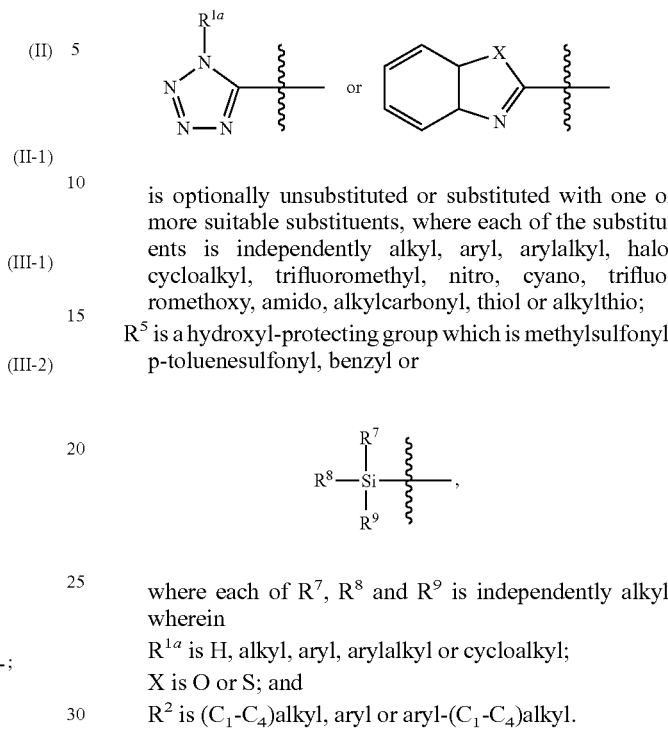

is optionally unsubstituted or substituted with one or more suitable substituents, where each of the substituents is independently alkyl, aryl, arylalkyl, halo, cycloalkyl, trifluoromethyl, nitro, cyano, trifluoromethoxy, amido, alkylcarbonyl, thiol or alkylthio;

$R^5$ is a hydroxyl-protecting group which is methylsulfonyl, p-toluenesulfonyl, benzyl or where each of $R^7$, $R^8$ and $R^9$ is independently alkyl, wherein $R^{1a}$ is H, alkyl, aryl, arylalkyl or cycloalkyl;

X is O or S; and $R^2$ is $(C_1$-$C_4)$alkyl, aryl or aryl-$(C_1$-$C_4)$alkyl.

* * * * *